(12) United States Patent
Watari (10) Patent No.: US 7,964,140 B2
(45) Date of Patent: *Jun. 21, 2011

(54) AUTOMATIC ANALYZER

(75) Inventor: Shigenori Watari, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/843,446

(22) Filed: Jul. 26, 2010

(65) Prior Publication Data

US 2010/0288830 A1 Nov. 18, 2010

Related U.S. Application Data

(63) Continuation of application No. 10/872,485, filed on Jun. 22, 2004, now Pat. No. 7,785,534.

(30) Foreign Application Priority Data

Jun. 23, 2003 (JP) .................................. 2003-177434

(51) Int. Cl.
*G01N 21/00* (2006.01)
*G01N 31/00* (2006.01)
*G01N 33/00* (2006.01)

(52) U.S. Cl. ................ 422/63; 422/62; 422/64; 422/65; 422/66

(58) Field of Classification Search ........................ None
See application file for complete search history.

(56) References Cited

U.S. PATENT DOCUMENTS

| 4,455,280 A | 6/1984 | Shinohara et al. |
| 4,678,752 A | 7/1987 | Thorne et al. |
| 4,795,613 A | 1/1989 | Azuma et al. |
| 4,919,887 A | 4/1990 | Wakatake |
| 5,051,238 A | 9/1991 | Umetsu et al. |
| 5,089,229 A | 2/1992 | Heidt et al. |
| 5,420,408 A | 5/1995 | Weyrauch et al. |
| 5,449,621 A | 9/1995 | Klein |
| 2002/0090737 A1 | 7/2002 | Levin et al. |
| 2002/0182108 A1 | 12/2002 | Ishihara et al. |
| 2003/0103023 A1 | 6/2003 | Ootsuka et al. |

FOREIGN PATENT DOCUMENTS

| EP | 0410645 A2 | 7/1990 |
| JP | 3274325 | 2/2002 |

*Primary Examiner* — Jill Warden
*Assistant Examiner* — Neil Turk
(74) *Attorney, Agent, or Firm* — Mattingly & Malur, PC

(57) ABSTRACT

An automatic analyzer is disclosed that has a structure capable of using reagent containers each having an ID, such as a barcode, attached either on the top surface or the undersurface thereof, or alternatively on each of them. This automatic analyzer, therefore, allows information about the reagent ID to be read or written at an arbitrary timing even if the mounting density of reagent containers of the automatic analyzer is increased, thereby improving the function and performance of the apparatus.

3 Claims, 9 Drawing Sheets

AUTOMATIC ANALYZER

This is a continuation application of U.S. application Ser. No. 10/872,485, filed Jun. 22, 2004, now U.S. Pat. No. 7,785,534, the contents of which are hereby incorporated by reference into this application.

BACKGROUND OF THE INVENTION

1. Field of the Invention

The present invention relates to a reagent dispensing system for an automatic analyzer that automatically performs a qualitative/quantitative analysis of a biological sample such as blood, urine, or the like, and an automatic analyzer using the same. More particularly, the present invention concerns an automatic analyzer that uses reagent containers each having an information recording medium on which information about a reagent contained in the reagent container is recorded, and that is capable of reliably reading the information recorded on the aforementioned information recording medium while allowing the reagent-container mounting density per unit area to be increased.

2. Description of the Related Art

The automatic analyzer that automatically performs a qualitative/quantitative analysis of a biological sample such as blood, urine, or the like, has become prevalent mainly in medical laboratories and large hospitals, since it can meet the expectations for improvement in the quantitativity of analysis result and the speedup of analysis. The measurement principle of the automatic analyzer is to mix a sample that changes in color as a result of reacting with a component to be analyzed, with a sample, and then to measure the change in the color of the sample. Conventionally, the measurement of this change in color has been performed by a laboratory technician using a calorimetric table, whereas in the automatic analyzer, the measurement of the change in color is performed by means of a photometer, thereby achieving improvement in the quantitativity of analysis result and the speedup of analysis.

In recent year, in order to improve the operator-friendliness of the apparatus, various techniques have been proposed. One of them is to record information, such as the kind of reagent, on an information recording medium such as a barcode label, and to automatically identify the kind of the reagent by reading this information recording medium. When the operator must input the kind of reagent into a computer, if the kind of reagent is inputted in error, there occurs a possibility of an erroneous analysis result being reported, whereas the method using the information recording medium as described above would be expected to reduce load upon the operator, and also decrease possibility of causing an error in analysis result.

With the diversification of analysis items, market demands an automatic analyzer capable of mounting thereon more reagents and simultaneously having a compact size. However, the barcode, which is the mainstream of conventional information recording media, is read by an optical manner, and therefore, mounting reagent containers at high density unfavorably inhibits the barcode from being read. To solve this problem, Japanese Patent No. 3274325 proposes to arrange reagent disks along respective circumferences of the double concentric circles, and simultaneously, in order to read the barcode of the reagent container on the inner peripheral side, this patent document proposes to provide a portion devoid of reagent in a row of reagent containers on the outer peripheral side, and read the barcode of the reagent container on the inner peripheral side, from the aforementioned portion. This method allows the enhancement of the mounting density of reagent containers and the identification of reagent by the barcode to be mutually compatible.

SUMMARY OF THE INVENTION

In the method disclosed in the above-described patent document, the disposition of the reagent containers placed on the outer peripheral side is limited because of the necessity for reading the barcode of the reagent container on the inner peripheral side. If the reagent disks are arranged in double concentric circles, it is deemed that the aforementioned limitation is not so big a problem. However, if the reagent disks are arranged in no less than triple concentric cylinders in order to increase the mounting density, a significant disadvantage might be caused.

Accordingly, it is an object of the present invention to provide an automatic analyzer that is capable of mounting reagent containers at a higher density while using reagent containers each having an information recording medium for identifying a reagent.

To achieve the above-described object, the present invention provides a reagent dispensing system that includes a reagent container for holding a reagent; a reagent cold-storage chamber for keeping a plurality of the reagent containers at a low temperature; a reagent dispensing device for sucking, from an arbitrary reagent container held in the reagent cold-storage chamber, a reagent in the reagent container. In this reagent dispensing system, the lid of the reagent cold-storage chamber is divided into at least two portions: a movable portion that is openable and closable, and that is used for taking out the reagent container; and an fixed portion that is non-openable and non-closable, and that is provided fixedly with respect to the cold-storage chamber. Herein, the fixed portion has an information reading section for reading information of a recording section that is provided to the reagent container, and that records information including information about the reagent in the reagent container.

In the reagent dispensing system according to the present invention, it is preferable that the recording section be disposed on the top surface of the reagent container.

In the reagent dispensing system according to the present invention, the recording section may exchange information with the information reading section by radio waves.

In the reagent dispensing system according to present invention, the fixed portion of the lid may have an opening for the reagent dispensing device to suck a reagent from the reagent container, and the information reading section may be disposed in the vicinity of the aforementioned opening.

In the reagent dispensing system according to present invention, the information reading section may read information of the information recording section of the reagent container immediately before the reagent dispensing device sucks a reagent from the reagent container, and the reagent dispensing device may suck a reagent after the aforementioned reagent has been checked to be sure that it is a desired reagent.

DESCRIPTION OF THE PREFERRED EMBODIMENTS

Typically, in the automatic analyzer, a barcode label, which can record information intended for identifying or necessary to manage a reagent, is attached on a side surface of a reagent container for storing a chemical agent used for analyzing components of a sample to be analyzed. A possible alternative way to read or write information is to provide the automatic analyzer with a recording medium that writes or reads information by an electric or magnetic method, or using a method combining these electric and magnetic methods. The barcode reader for reading information stored in a storage medium such as the aforementioned barcode label, or the writing/reading mechanism making use of an electrical or magnetic coupling, or a method combining the electric and magnetic coupling, is provided on a side surface of the reagent container. Each of them reads manually or automatically information about the kind of reagent and information necessary for analysis from the side direction of the reagent container when a reagent bottle is set in the apparatus. Alternatively, when powering on the apparatus, re-reading is automatically performed as a general rule in order to identify the reagent already mounted.

In the automatic analysis, in order to perform analyses of more items, it is required to mount more kinds of reagents, and therefore, the number of reagent containers mounted must be increased. On the other hand, it is desired that the overall size of the apparatus be reduced from the viewpoint of the floor area of a facility. Hence, it follows that the mounting density of reagent containers must be enhanced.

Figure 4A:
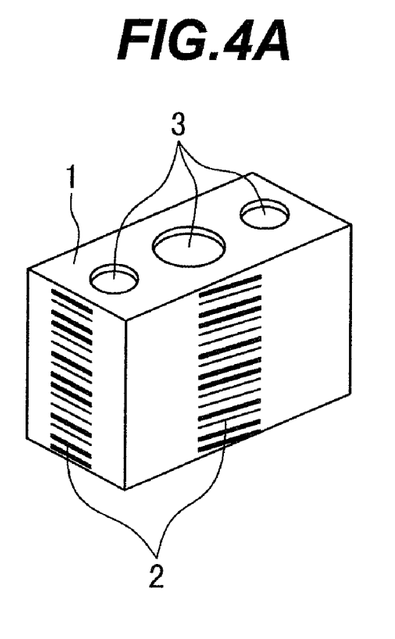
FIGS. 4A and 4B are each a schematic view of a conventional reagent container.
Figure 4B:
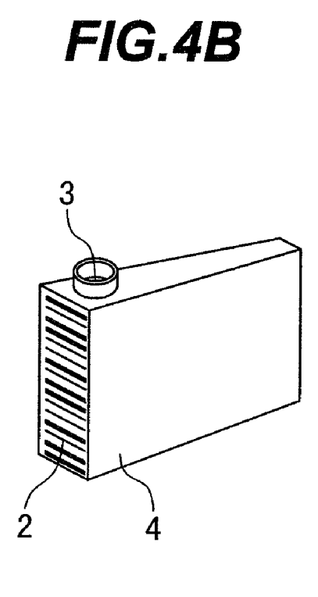
Figure 5:
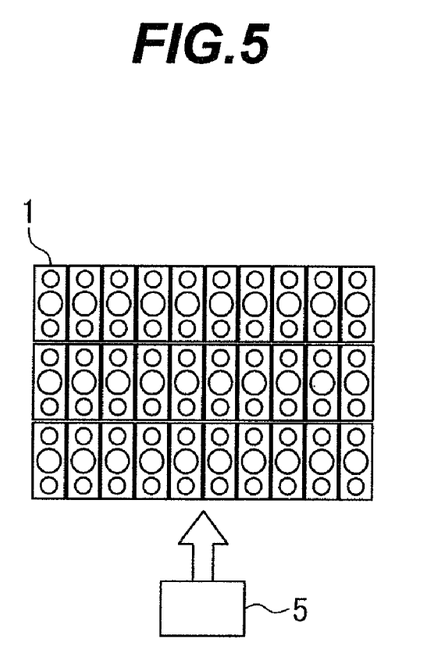
FIG. 5 shows an example of an efficient layout of reagent containers.

For that purpose, as shown in FIG. 5, the distance between reagent containers must be reduced to a minimum. However, if the configuration shown in FIG. 5 is adopted, when attempting to perform the re-reading of the reagent management information at power-on using the method in which information is provided on at least one side surface of a reagent container as conventional examples (see FIGS. 4A and 4B), a user has no alternative but to once take out the reagent container, and after transferring it to another place, perform the re-reading of the information. This unfavorably requires much time.

Figure 6A:
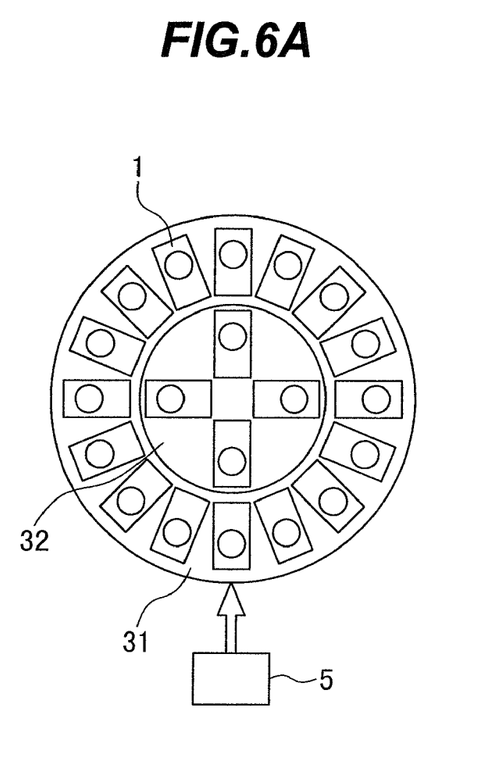
FIGS. 6A and 6B are each a top view showing an example of layout of reagent containers on a reagent disk.
Figure 6B:
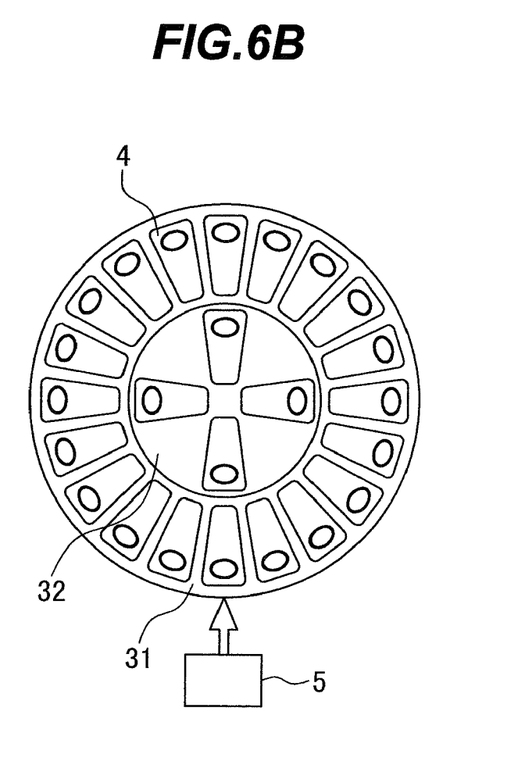

Typically, in the method in which information is provided on a side surface of a reagent container, a way in which reagent containers are arranged in circles, and in which a reading/writing mechanism is provided outside the reagent containers arranged in circles as shown in FIGS. 6A and 6B, is employed. However, when the reagent container has a rectangular parallelepiped shape or a cubic shape, a reagent housing case having a circular shape would have much useless space. To solve this problem, fan-shaped reagent containers are used for some apparatuses. As shown in FIGS. 6A and 6B, when reagent containers are housed by dividing them into ones on the outer peripheral side and ones on the inner peripheral side in order to increase the number of mounted reagent containers, a barcode reader, which utilizes light, is used to read information about reagent containers disposed along the inner periphery. In this case, the distance between the reagent containers disposed along the outer periphery must be widened up to a distance that allows the barcodes on the reagent containers on the inner peripheral side to be read. The above-described structure, therefore, reduces the mounting density of reagent containers.

Hereinafter, embodiments according to the present invention will be described in detail with reference to the accompanying drawings.

First Embodiment

Figure 1A:
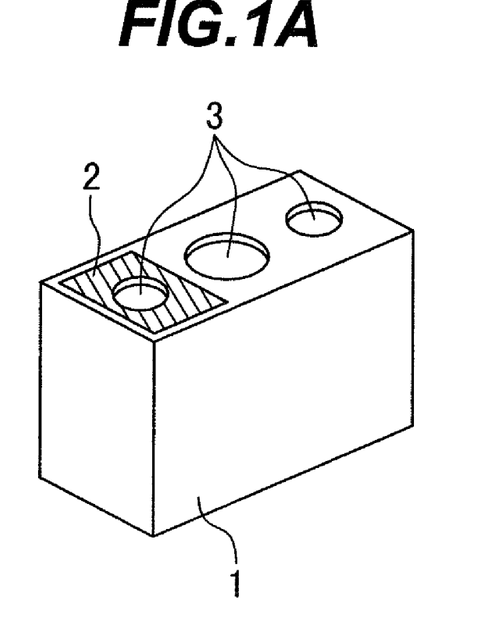
FIGS. 1A, 1B, and 1C are each a schematic view of a reagent container to be mounted on an automatic analyzer, according to a first embodiment of the present invention.
Figure 1B:
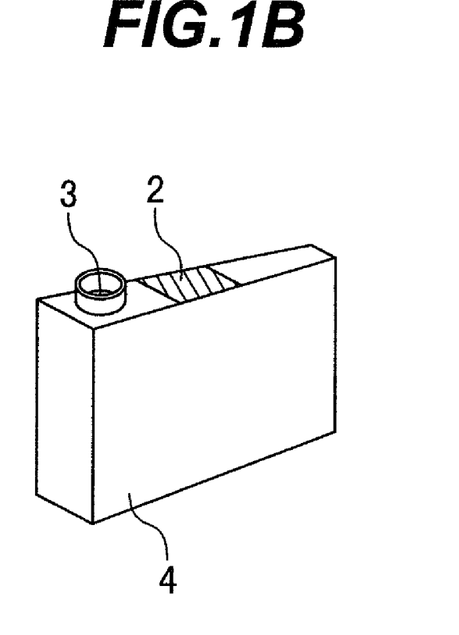
Figure 1C:
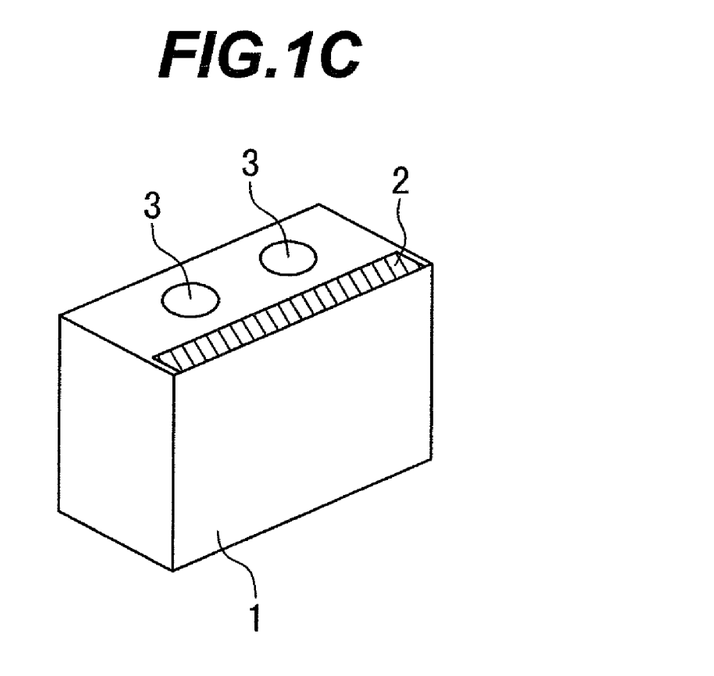

FIGS. 1A, 1B, and 1C are each a schematic view of a reagent container 1 for storing a reagent necessary for analysis and mounted on an automatic analyzer, according to a first embodiment of the present invention. Depending upon a specification of the apparatus, the reagent container 1 has a rectangular parallelepiped shape or a fan shape. A reagent ID 2 that can store information necessary for the management of reagent is attached on the top surface of the reagent container 1. The reagent ID 2 is constituted of a barcode, semiconductor storage medium, magnetic storage medium, optical storage medium, or the like.

Figure 2:
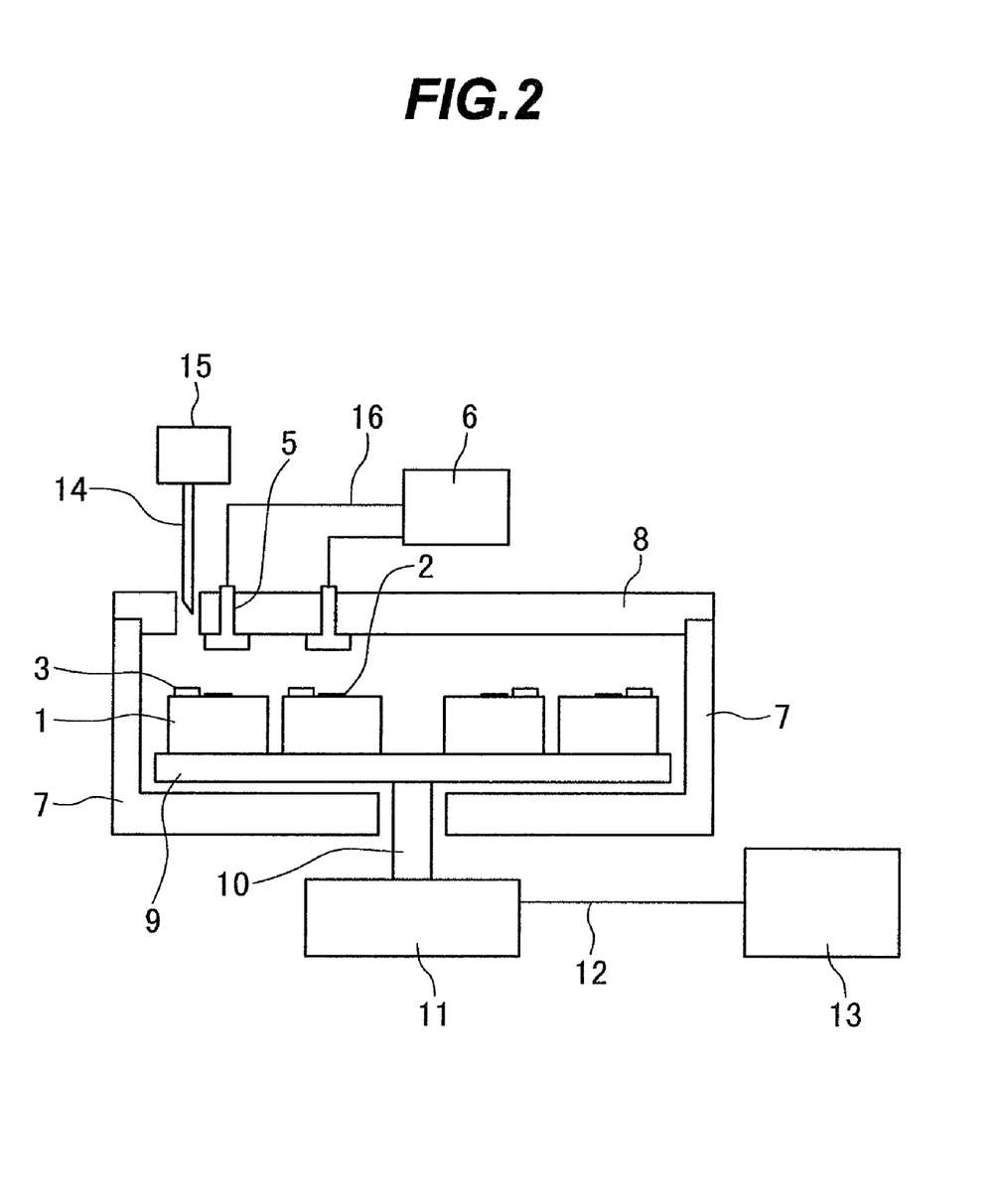
FIG. 2 is a sectional view of a reagent cold-storage chamber of the automatic analyzer according to the present invention.
Figure 3:
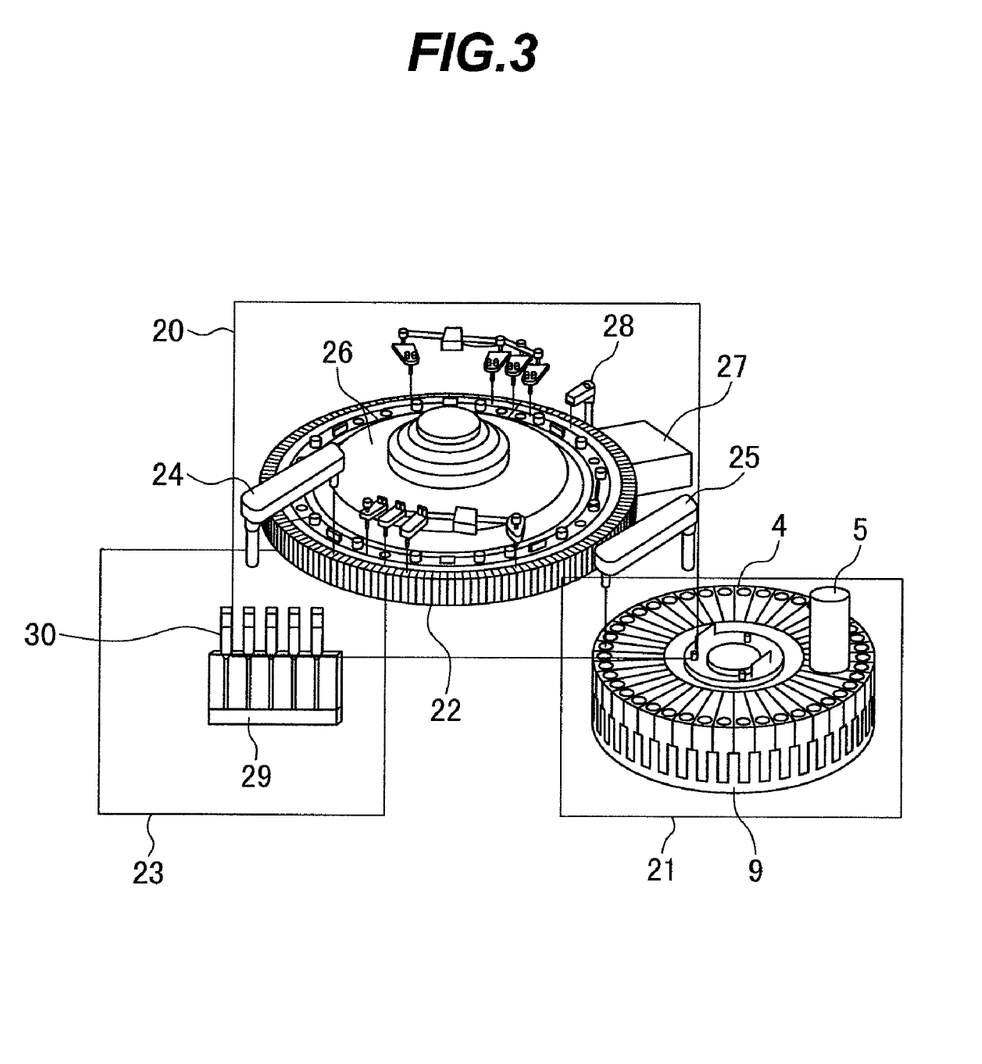
FIG. 3 is a schematic view of the automatic analyzer according to the present invention.

As shown in FIG. 3, the reagent container 1 is mounted on a reagent disk 9 in a reagent storage section 21. The reagent storage section 21 according to the first embodiment is shown in FIG. 2. In FIG. 2, a plurality of reagent containers 1 can be mounted on a reagent disk 21 having a circular shape. The reagent container 1 and the reagent disk 9 are thermally insulated by a reagent cold-storage chamber 7 and the lid 8 of the reagent cold-storage chamber 7. A plurality of reading/writing mechanisms 5 is provided to the lid 8 of the reagent cold-storage chamber 7, and can read or write information that is necessary for the analysis of a sample, and that is stored in the reagent ID 2 attached on the top surface of the reagent container 1, by a non-contact method or a contact method through the use of electromagnetic waves, magnetism, light, or the like. The information about a reagent that is necessary for analysis and that has been read by the reading/writing mechanisms 5 is sent to an information control section 6 by a communication line 16, and it is utilized for an analytical operation by the automatic analyzer. The information control section 6 writes, into the reagent ID 2, reagent management information that has been occurred as a result of the present automatic analyzer operating and that is represented by the number of times of reagent usage, reagent unsealing date, reagent expiration date and the like, by means of the reading/writing mechanisms 5. The reagent disk 9 rotates in the horizontal direction under the drive from a motor 11 for rating the reagent disk 9, and transfers the reagent container 1 to a predetermined position that allows a reagent inside the reagent container 1 to be sucked by a reagent nozzle 14 of a reagent dispensing device 15, or a predetermined position that allows information necessary for analysis and stored inside the reagent ID 2 to be read or written by the reading/writing mechanisms 5. As shown in FIG. 3, the automatic analyzer with the above-described features dispenses a sample stored in a sample container 30 mounted on a sample rack 29 situated in a sampler section 23 into a reaction cell 22 in an analysis section 20 by a sample probe 24. The automatic analyzer then dispenses a reagent in the reagent storage section 21 into the aforementioned reaction cell 22 by a reagent probe 25. Thereafter, the automatic analyzer stirs and mixes the sample and the reagent by a stirring mechanism 28, and detects the process of chemical reaction between the sample and the reagent and analyzes components included in the sample by a detector 27. In this embodiment, the reagent ID 2 is attached on the top surface of the reagent container 1. However, the reagent ID 2 may be attached on the undersurface of the reagent container 1, and the reading/writing mechanisms 5 may also be disposed below the reagent containers 1. Alternatively, the reagent ID 2 may be attached both on the top surface and undersurface of the reagent container 1.

Second Embodiment

Figure 7:
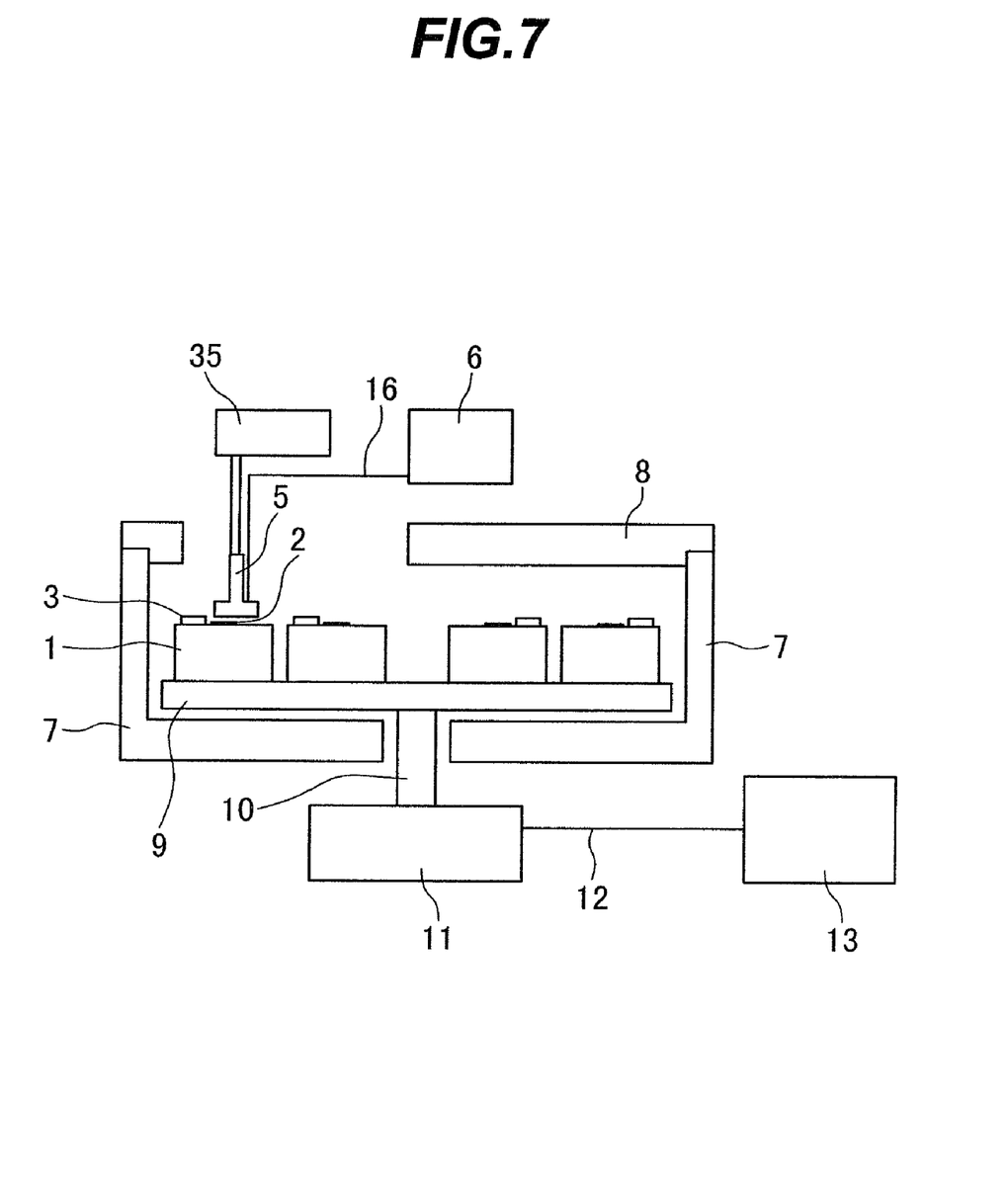
FIG. 7 is a sectional view of a reagent cold-storage chamber of an automatic analyzer according to a second embodiment of the present invention, the reagent cold-storage chamber having the reagent container layout shown in FIG. 6A or 6B.

FIG. 7 is a schematic view of an automatic analyzer according to a second embodiment of the present invention, wherein reagent containers 1 are arranged along the inner periphery and the outer periphery of the reagent disk 9 in a concentric manner as shown in FIGS. 6A and 6B, in order to increase the number of reagent containers mounted on the automatic analyzer 1. In this embodiment, the automatic analyzer has a transfer mechanism 35 for the reading/writing mechanism 5 in order to transfer the reading/writing mechanism 5. This transfer mechanism 35 for the reading/writing mechanism 5 transfers the reading/writing mechanism 5 in the X, Y, and Z axis directions, and the rotational direction, whereby the reading/writing mechanism 5 is transferred to a position that allows information necessary for analysis, and stored inside the reagent ID 2 on the reagent container 1 situated at an arbitrary position, to be read by the reading/writing mechanism 5.

When the moving range of the transfer mechanism 35 for the reading/writing mechanism 5 is limited, or when the moving distance or the moving time thereof must be reduced, the reagent disk 9 in this embodiment horizontally rotates under drive from the motor 11 for rotating the reagent disk 9, and transfers the reagent container 1 to a position where a reagent inside the reagent container 1 is to be sucked by the reagent nozzle 14, or a position that allows information necessary for analysis and stored inside the reagent ID 2 to be read or written by the reading/writing mechanism 5.

Third Embodiment

Figure 8:
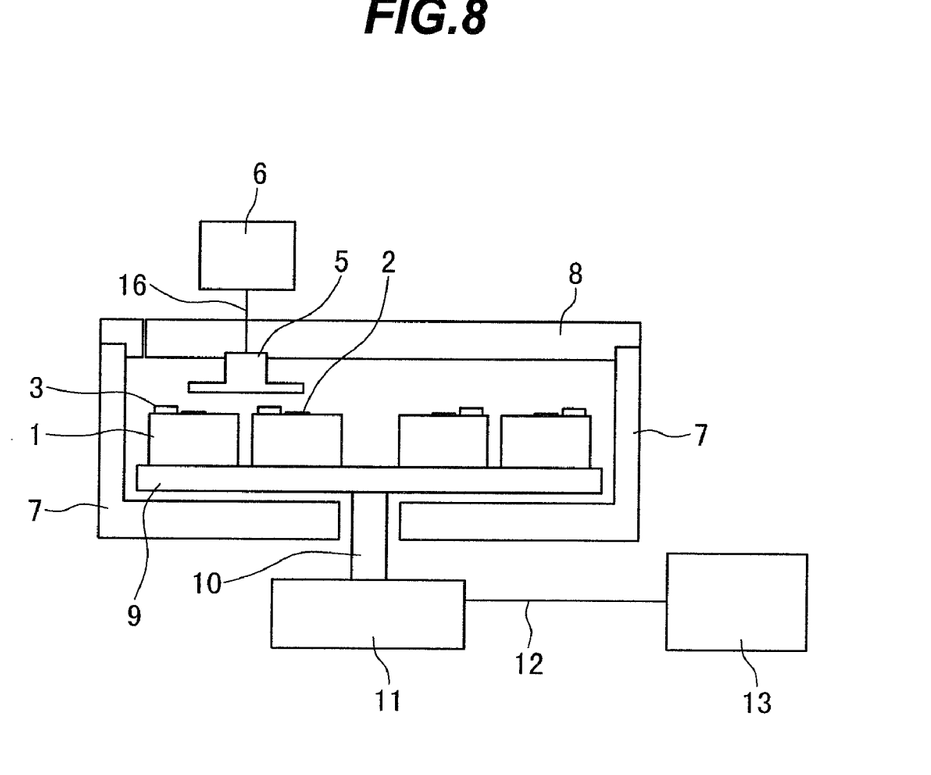
FIG. 8 is a sectional view of a reagent cold-storage chamber of an automatic analyzer according to a third embodiment of the present invention, the reagent cold-storage chamber having the reagent container layout shown in FIG. 6A or 6B.

FIG. 8 is a schematic view of an automatic analyzer according to a third embodiment of the present invention intended for the reduction in the number of the reading/writing mechanisms 5 in the first embodiment. In this embodiment, the detection section of a reading/writing mechanism 5 located above a rotary-type reagent disk 9 and reagent containers 1 has a size long enough to straddle reagent IDs 2 on a plurality of reagent containers, and reads a single reagent ID 2 or a plurality of reagent IDs 2 without the need for the rotation of the reagent disk 9 and the movement of the reading/writing mechanism 5.

Fourth Embodiment

Figure 9:
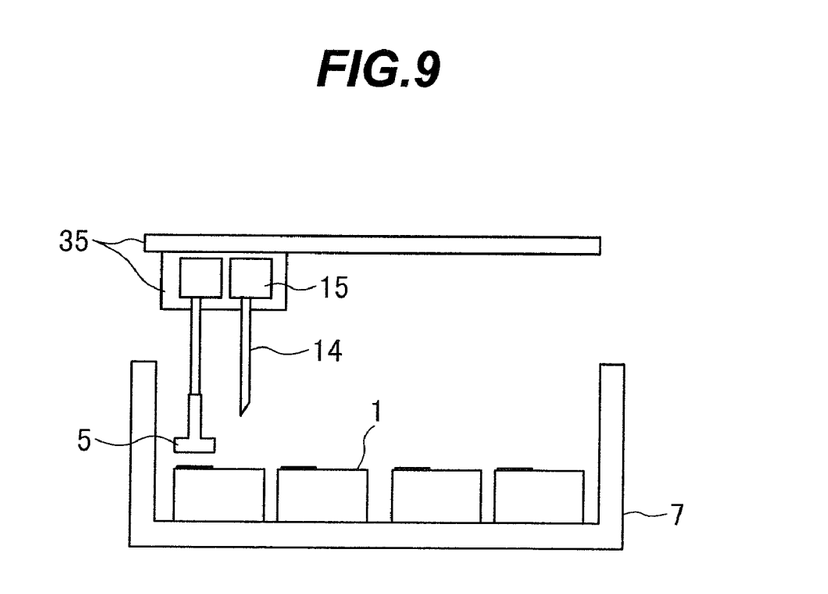
FIG. 9 is a sectional view of a reagent cold-storage chamber of an automatic analyzer according to a fourth embodiment of the present invention, the reagent cold-storage chamber having the reagent container layout shown in FIG. 5.

FIG. 9 is a schematic view of an automatic analyzer according to a fourth embodiment of the present invention, wherein, for the purpose of increasing the number of reagent containers 1 mounted on the automatic analyzer, the reagent containers 1 are arranged in a manner as shown in FIG. 5, i.e., not in a concentric manner. In this embodiment, there is not provided a rotary-type reagent disk 9 as present in FIGS. 2, 7, and 8, and the reagent containers 1 are provided in the reagent cold-storage chamber 7 in a lattice-like arrangement. The reading/writing mechanisms 5 is transferred by the transfer mechanism 35 for the reading/writing mechanism 5 to a position that allows information necessary for analysis, and stored inside the reagent ID 2 on the reagent container 1 that is situated in an arbitrary position out of the reagent containers 1 disposed in fixed positions in the automatic analyzer, to be read by the reading/writing mechanism 5.

Fifth Embodiment

Figure 10:
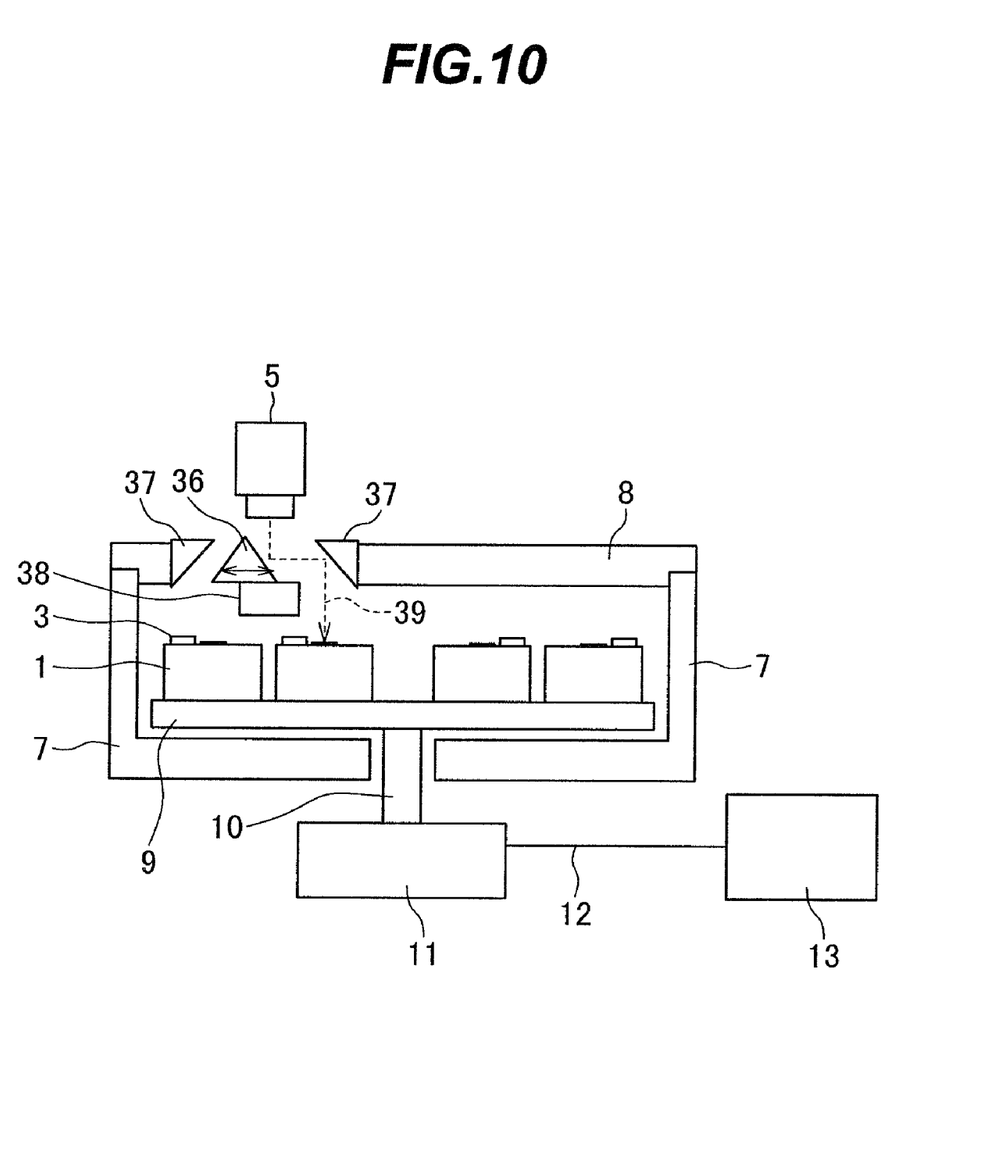
FIG. 10 is a sectional view of a reagent cold-storage chamber of an automatic analyzer according to a fifth embodiment of the present invention, the reagent cold-storage chamber being equipped with a mechanism having mirrors.
Figure 11:
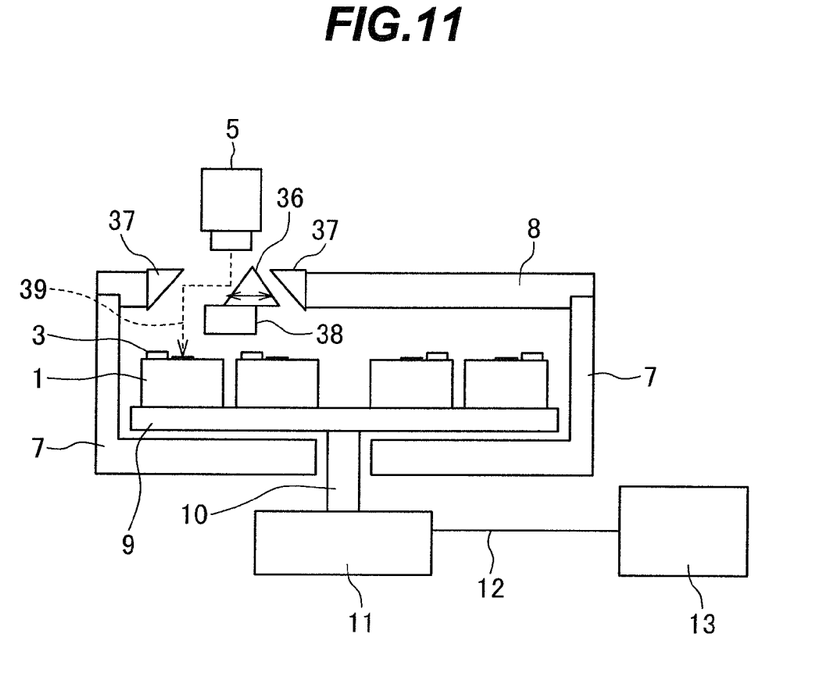
FIG. 11 is another sectional view of the reagent cold-storage chamber of the automatic analyzer according to the fifth embodiment of the present invention, the reagent cold-storage chamber being equipped with the mechanism having the mirrors.

FIGS. 10 and 11 are each a schematic view of an automatic analyzer according to a fifth embodiment of the present invention in which, for the purpose of increasing the number of reagent containers 1 mounted on the automatic analyzer, the reagent containers are arranged in a concentric manner along the outer periphery and the inner periphery of the reagent disk 9 as illustrated in FIGS. 6A and 6B, and which is intended for the reduction in the number of the reading/writing mechanisms 5. The reading/writing mechanism 5 used in this embodiment is a reading mechanism for reading a reagent ID 2 using light represented by a barcode reader. To the lid 8 of the reagent cold-storage chamber 7, one reading/writing mechanism 5, two fixed mirrors 37, and one movable mirror 36 are affixed. The movable mirror 36 is formed into a pent-roof shape by combining two mirrors, with its reflecting surface facing the outside. This movable mirrors 37 are fixed to a mirror operating mechanism 38, and moves toward or away from the fixed mirrors 37 in accordance with a movement of the mirror operating mechanism 38. Above the reagent containers on the inner peripheral side and the outer peripheral side of the reagent disk 9, the two fixed mirrors 37 are affixed to the lid 8 of the reagent cold-storage chamber 7. The reading/writing mechanisms 5 is located substantially above the top of the movable mirror 36, which is formed into a pent-roof shape by combining two mirrors. These reading/writing mechanisms 5, fixed mirrors 37, and movable mirror 36 each have a disposition that allows information necessary for analyzing a sample, and stored in the reagent ID 2 attached on the top surface of the reagent container 1, to be sent to the reading/writing mechanisms 5 through an optical path 39. The movable mirror 36 has a structure so as to be moved by the mirror operating mechanism 38 to a position where, as shown in FIG. 10, information that is necessary for analyzing a sample, and that is stored in the reagent ID 2 attached on the top surface of the reagent container 1 on the inner peripheral side of the reagent disk 9, is to be read, or to a position where, as shown in FIG. 11, information that is necessary for analyzing a sample, and that is stored in the reagent ID 2 attached on the top surface of the reagent container 1 on the outer peripheral side of the reagent disk 9, is to be read.

Sixth Embodiment

Figure 12:
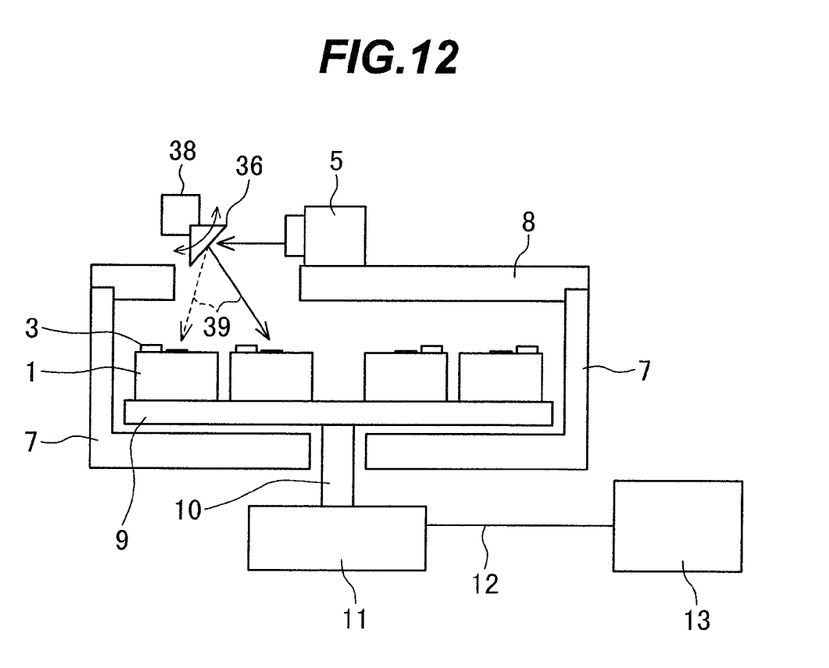
FIG. 12 is a sectional view of a reagent cold-storage chamber of an automatic analyzer according to a sixth embodiment of the present invention, the reagent cold-storage chamber being equipped with a mechanism having a mirror.

FIG. 12 is a schematic view of an automatic analyzer according to a sixth embodiment of the present invention in which, for the purpose of increasing the number of reagent containers 1 mounted on the automatic analyzer, the reagent containers are arranged in a concentric manner along the outer periphery and the inner periphery of the reagent disk 9 as illustrated in FIGS. 6A and 6B, and which is intended for the reduction in the number of the reading/writing mechanisms 5. The reading/writing mechanism 5 used in this embodiment is a reading mechanism for reading a reagent ID 2 using light represented by a barcode reader. To the lid 8 of the reagent cold-storage chamber 7 or above it, one reading/writing mechanism 5, and basically one movable mirror 36 are affixed. The movable mirror 36 is fixed to a mirror operating mechanism 38, and has a structure so as to be able to change the orientation of its reflecting surface in accordance with a movement of the mirror operation mechanism 38. These reading/writing mechanisms 5 and movable mirror 36 each have a disposition that allows information necessary for analyzing a sample, and stored in the reagent ID 2 attached on the top surface of the reagent container 1, to be sent to the reading/writing mechanisms 5 through an optical path 39. Also, as shown in FIG. 12, the movable mirror 36 has a structure so as to be moved by a mirror operating mechanism 38 to a position where information that is necessary for analyzing a sample and that is stored in the reagent ID 2 attached on the top surface of the reagent container 1 on the inner peripheral side of the reagent disk 9, is to be read, or to a position where information that is necessary for analyzing a sample and that is stored in the reagent ID 2 attached on the top surface of the reagent container 1 on the outer peripheral side of the reagent disk 9, is to be read.

As is evident from the foregoing, according to the present invention, it is possible to provide an automatic analyzer that allows the apparatus cost to be reduced by an inexpensive mechanism, and that enables the throughput and the number of processing items of the apparatus to be increased.

What is claimed is:

1. An automatic analyzer comprising:
a reagent cold-storage chamber for holding a plurality of reagent containers arranged in a plurality of circular rows in a concentric manner;
a reagent dispensing device for sucking a reagent from one of the plurality of the reagent containers held in the reagent cold-stage chamber;
a recording section arranged at a top surface of each of said reagent containers, said recording section recording information including information of a reagent in the reagent container;
a lid arranged at an upper portion of the reagent cold-stage chamber;
a barcode reader arranged at the lid, said barcode reader reading information recorded in the recording section arranged at the top surface of each of the reagent containers;
a detector which detects a chemical reaction between a sample and the reagent; and
one or more reflectors for bending light from the barcode reader to the recording section,
wherein the barcode reader reads the information recorded on the recording section with the light bent by the one or more reflectors.

2. The automatic analyzer according to claim 1, wherein said one or more reflectors are arranged at the lid, each of said one or more reflectors being arranged at each circular row of reagent containers, at least one of said one or more reflectors being a movable mirror for reflecting the light from the barcode reader toward any of said one or more reflectors.

3. The automatic analyzer according to claim 1, wherein said one or more reflectors includes an angle changing means for changing an orientation of the light from the barcode reader toward one of said circular rows of the reagent containers.

* * * * *